US012767720B2

(12) United States Patent
Yu et al.

(10) Patent No.: US 12,767,720 B2
(45) Date of Patent: Oct. 20, 2026

(54) PREPARATION AND USE OF ANTI-FSHR ANTIBODY AND ANTIBODY-DRUG CONJUGATE THEREOF

(71) Applicant: CANWELL (GZ) BIOTECH LIMITED, Guangzhou (CN)

(72) Inventors: Ninghui Yu, Guangzhou (CN); Xuliang Jiang, Guangzhou (CN)

(73) Assignee: CANWELL (GZ) BIOTECH LIMITED, Guangzhou (CN)

( * ) Notice: Subject to any disclaimer, the term of this patent is extended or adjusted under 35 U.S.C. 154(b) by 686 days.

(21) Appl. No.: 18/255,459

(22) PCT Filed: Nov. 18, 2021

(86) PCT No.: PCT/CN2021/131515

§ 371 (c)(1),
(2) Date: Jun. 1, 2023

(87) PCT Pub. No.: WO2022/116853

PCT Pub. Date: Jun. 9, 2022

(65) Prior Publication Data

US 2024/0043548 A1 Feb. 8, 2024

(30) Foreign Application Priority Data

Dec. 4, 2020 (CN) ......................... 202011417088.9

(51) Int. Cl.

| | |
|---|---|
| ***A61K 39/395*** | (2006.01) |
| ***A61K 47/68*** | (2017.01) |
| ***A61P 35/00*** | (2006.01) |
| ***C07K 16/28*** | (2006.01) |

(52) U.S. Cl.

CPC ...... *C07K 16/2869* (2013.01); *A61K 39/3955* (2013.01); *A61K 47/6803* (2017.08); *A61K 47/68031* (2023.08); *A61K 47/6849* (2017.08); *A61K 47/6851* (2017.08); *A61P 35/00* (2018.01); *C07K 2317/92* (2013.01)

(58) Field of Classification Search

CPC ............ A61K 39/3955; A61K 47/6849; A61K 47/6851; A61K 47/6803; C07K 16/2869

See application file for complete search history.

(56) References Cited

U.S. PATENT DOCUMENTS

2020/0010556 A1 1/2020 Ghinea

FOREIGN PATENT DOCUMENTS

| | | | | |
|---|---|---|---|---|
| CN | 109661239 A | | 4/2019 | |
| CN | 110072542 A | | 7/2019 | |
| EP | 3378872 A1 | * | 9/2018 | ......... C07K 16/2869 |
| WO | WO 93/20199 A1 | | 10/1993 | |
| WO | WO-2017035430 A2 | * | 3/2017 | ............. C07K 16/40 |
| WO | WO-2020033797 A1 | * | 2/2020 | .............. A61P 35/00 |

OTHER PUBLICATIONS

International Search Report issued Feb. 15, 2022 in PCT/CN2021/131515 filed on Nov. 18, 2021, 5 pages.

Xi et al., "Rapid Generation of Anti-FSHR Nanobody by CDR3 Affinity Transfer Approach", Xinjinag Agricultural Sciences, vol. 54, No. 7, Dec. 31, 2017, 7 pages.

Chen et al., "Crystal Structure of a TSH Receptor Monoclonal Antibody: Insight Into Graves' Disease Pathogenesis", Molecular Endocrinology, vol. 29, No. 1, Jan. 2015, 9 pages.

Chrusciel et al., "Extragonadal FSHR Expression and Function—Is it Real?", Frontiers in Endocrinology, vol. 10, Feb. 4, 2019, 10 pages.

* cited by examiner

*Primary Examiner* — Xiaozhen Xie

(74) *Attorney, Agent, or Firm* — Merchant & Gould P.C.; Daniel J. Pereira

(57) ABSTRACT

An antibody or an antigen-binding fragment thereof that specifically binds to human follicle-stimulating hormone receptor (FSHR), and an antibody-drug conjugate thereof are disclosed. The antibody or the antigen-binding fragment thereof contains a variable region comprising one, two, three, four, five or six CDRs with the amino acid sequences shown in SEQ ID NOs: 6, 7, 8, 10, 11 and 12. Also provided are methods for the preparation and use of the anti-FSHR antibody and the antibody-drug conjugate thereof. The provided anti-FSHR antibody and the antibody-drug conjugate thereof have broad application prospects in detecting, screening, preventing, and treating cancers.

17 Claims, 4 Drawing Sheets

Specification includes a Sequence Listing.

PREPARATION AND USE OF ANTI-FSHR ANTIBODY AND ANTIBODY-DRUG CONJUGATE THEREOF

CROSS REFERENCE TO RELATED APPLICATIONS

This application is a National Stage entry under 35 U.S.C. § 371 of PCT/CN2021/131515, filed on Nov. 18, 2021, and claims priority to Chinese Patent Application No. 202011417088.9, filed on Dec. 4, 2020, the entire contents of which are incorporated herein by reference.

TECHNICAL FIELD

The present invention belongs to the field of biotechnology, and relates to preparation and use of an anti-FSHR antibody and an antibody-drug conjugate thereof.

BACKGROUND

Human follicle-stimulating hormone receptor (FSHR) is an 80 kD G-protein coupled membrane receptor. The FSHR extracellular domain contains a 9-leucine-rich-repeat (LRR) domain, an extracellular hinge loop, a 7-helical transmembrane domain, and a cytoplasmic domain. The LRR domain is responsible for high-affinity binding of FSH, the hinge loop for receptor activation and the transmembrane and cytoplasmic domains for receptor signaling.[1-4]

The human FSHR is expressed primarily in granulosa cells of the ovary and the Sertoli cells of the testis.[5] Recombinant follicle stimulating hormone (FSH), the naturally protein ligand of FSHR, has been clinically used in treatment in female and male infertilities. Several FSHR small molecule allosteric modulators have also been discovered[6-9]

FSHR expression in several extragonadal normal and tumorous tissues has been recently detected. FSHR is transcribed in human female reproductive tract and placenta,[10] osteoclasts,[11] adipocytes,[12] chondrocytes,[13] benign prostatic hyperplasia and prostate cancer,[13] and ovarian cancer.[14] FSH receptor is also expressed by endothelial cells in tissue samples from patients with a wide range of tumors.[15] The tumors were located in prostate, breast, colon, pancreas, urinary bladder, kidney, lung, liver, stomach, testis, and ovary.

Due to the common marker of FSHR in peritumoral vessel, prostate cancer and ovarian cancer, anti-FSHR humanized antibodies should be in principle applicable to a wide range of tumor types. Currently, there is no approved antibody drug against FSHR for cancer treatment in the market. There is a clear need to invent new anti-FSHR antibodies that can effectively treat various cancers. Therefore, it is urgent to develop a new anti-FSHR monoclonal antibody and its antibody-drug conjugate (ADC) that can be used for detecting, screening and treating cancers with lower toxic and side effects and better clinical efficacy. This will give patients more drug options.

REFERENCES

1. Jiang, X. et al. Structural predictions for the ligand-binding region of glycoprotein hormone receptors and the nature of hormone-receptor interactions. *Structure* 3, 1341-1353 (1995).
2. Jiang, X. et al. Structure of follicle-stimulating hormone in complex with the entire ectodomain of its receptor. *Proc. Natl. Acad. Sci.* 109, 12491-12496 (2012).
3. Jiang, X., Dias, J. A. & He, X. Structural biology of glycoprotein hormones and their receptors: Insights to signaling. *Mol. Cell. Endocrinol.* 382, 424-451 (2014).
4. Jiang, X. et al. Evidence for follicle-stimulating hormone receptor as a functional trimer. *J. Biol. Chem.* 289, 14273-14282 (2014).
5. Sprengel, R., Braun, T., Nikolics, K., Segaloff, D. L. & Seeburg, P. H. The Testicular Receptor for Follicle Stimulating Hormone: Structure and Functional Expression of Cloned cDNA. *Mol. Endocrinol.* 4, 525-530 (1990).
6. Henry, N. Y. et al. Discovery of substituted benzamides as follicle stimulating hormone receptor allosteric modulators. *Bioorg. Med. Chem. Lett.* 24, 2168-2172 (2014).
7. Sriraman, V. et al. Investigation of a thiazolidinone derivative as an allosteric modulator of follicle stimulating hormone receptor: evidence for its ability to support follicular development and ovulation. Biochem. *Pharmacol* 89, 266-275 (2014).
8. Nataraja, S. G., Yu, H. N. & Palmer, S. S. Discovery and development of small molecule allosteric modulators of glycoprotein hormone receptors. *Front. Endocrinol.(Lausanne).* 6, 142 (2015).
9. Vannier, B., Loosfelt, H., Meduri, G., Pichon, C. & Milgrom, E. Anti-human FSH receptor monoclonal antibodies: immunochemical and immunocytochemical characterization of the receptor. *Biochemistry* 35, 1358-1366 (1996).
10. Stilley, J. A. W. et al. FSH receptor (F SEM) expression in human extragonadal reproductive tissues and the developing placenta, and the impact of its deletion on pregnancy in mice. *Biol. Reprod.* 91, 71-74 (2014).
11. Sun, L. et al. FSH Directly Regulates Bone Mass. *Cell* 125, 247-260 (2006).
12. Liu, P. et al. Blocking FSH induces thermogenic adipose tissue and reduces body fat. *Nature* 546, 107 (2017).
13. Kong, D. et al. Expression of FSHR in chondrocytes and the effect of FSH on chondrocytes. *Biochem. Biophys. Res. Commun.* 495, 587-593 (2018).
14. Perales-Puchalt, A. et al. Follicle-stimulating hormone receptor is expressed by most ovarian cancer subtypes and is a safe and effective immunotherapeutic target. *Clin. Cancer Res.* 23, 441-453 (2017).
15. Radu, A. et al. Expression of follicle-stimulating hormone receptor in tumor blood vessels. *N. Engl. J. Med.* 363, 1621-1630 (2010).

SUMMARY OF THE INVENTION

In one aspect, the present invention provides an antibody or an antigen-binding fragment thereof, wherein the antibody or antigen-binding fragment thereof comprises a variable region and specifically binds to human follicle-stimulating hormone receptor FSHR, and comprises one, two, three, four, five or six CDRs selected from the following amino acid sequences: SEQ ID NOs: 6, 7, 8, 10, 11 and 12.

In some embodiments, in the antibody or antigen-binding fragment thereof, the antibody or the antigen-binding fragment thereof comprises a light chain variable region and/or a heavy chain variable region, and the antibody or the antigen-binding fragment thereof comprises one, two or three light chain CDRs selected from the following amino acid sequences: SEQ ID NOs: 6, 7 and 8; and/or, the antibody or the antigen-binding fragment thereof comprises one, two or three heavy chain CDRs selected from the following amino acid sequences: SEQ ID NOs: 10, 11 and 12.

In some embodiments, in any one of the antibodies or the antigen-binding fragments thereof mentioned above, the antibody or the antigen-binding fragment thereof comprises light chain CDRs with the amino acid sequences shown in SEQ ID NOs: 6, 7 and 8, and heavy chain CDRs with the amino acid sequences shown in SEQ ID NOs: 10, 11 and 12.

In some embodiments, the antibody or the antigen-binding fragment thereof is an isolated antibody or an antigen-binding fragment thereof.

In some embodiments, the antibody or the antigen-binding fragment thereof is a murine antibody, a chimeric antibody, a human antibody, a humanized antibody or an antigen-binding fragment thereof.

In some embodiments, in any one of the antibodies or the antigen-binding fragments thereof mentioned above, the antibody or the antigen-binding fragment thereof comprises a light chain variable region and a heavy chain variable region;

wherein the light chain variable region comprises the amino acid sequence shown in SEQ ID NO: 5, or an amino acid sequence with at least 90% identity with the amino acid sequence shown in SEQ ID NO: 5, or an amino acid sequence with one or more conservative amino acid substitutions compared with the amino acid sequence shown in SEQ ID NO: 5; and/or, the heavy chain variable region comprises the amino acid sequence shown in SEQ ID NO: 9, or an amino acid sequence with at least 90% identity with the amino acid sequence shown in SEQ ID NO: 9, or an amino acid sequence with one or more conservative amino acid substitutions compared with the amino acid sequence shown in SEQ ID NO: 9.

In some embodiments, the antibody or the antigen-binding fragment thereof is a mouse IgG class, which is selected from IgG1 subclass, IgG2A subclass, IgG2B subclass, IgG2C subclass or IgG3 subclass, and may be humanized by conventional methods.

In some embodiments, in any one of the antibodies or the antigen-binding fragments thereof mentioned above, the antibody or the antigen-binding fragment thereof comprises a light chain and a heavy chain;

wherein the light chain comprises the amino acid sequence shown in SEQ ID NO: 3, or an amino acid sequence with at least 90% identity with the amino acid sequence shown in SEQ ID NO: 3, or an amino acid sequence with one or more conservative amino acid substitutions compared with the amino acid sequence shown in SEQ ID NO: 3; and/or, the heavy chain comprises the amino acid sequence shown in SEQ ID NO: 4, or an amino acid sequence with at least 90% identity with the amino acid sequence shown in SEQ ID NO: 4, or an amino acid sequence with one or more conservative amino acid substitutions compared with the amino acid sequence shown in SEQ ID NO: 4.

In another aspect, the present invention further provides a variant of any one of the antibodies or the antigen-binding fragments thereof mentioned above, comprising no more than 10 amino acid substitutions, deletions and/or additions, such as one, two or three conservative amino acid substitutions, deletions and/or additions, e.g., the amino acid substitutions, deletions and/or additions are in an FR region, or at least one substitution, deletion and/or addition is in a CDR region.

In some embodiments, the amino acid substitutions, deletions and/or additions are achieved by nucleotide mutation via a method selected from the group consisting of: oligonucleotide-mediated site-directed mutagenesis, cassette mutagenesis, degenerate oligonucleotide primed PCR, error-prone PCR, DNA shuffling and use of a bacterial mutator.

In another aspect, the present invention further provides a biological material related to any one of the antibodies or the antigen-binding fragments thereof mentioned above or the variants mentioned above, which is the following B1) or B2):

B1) a nucleic acid molecule encoding any one of the antibodies or the antigen-binding fragments thereof mentioned above or the variants mentioned above; and B2) an expression cassette, a recombinant vector, a recombinant cell or a recombinant microorganism containing the nucleic acid molecule of B1).

In some embodiments, in the above biological material, the nucleic acid molecule of B1) may be DNA, such as cDNA, genomic DNA or recombinant DNA; and the nuucleic acid molecule may also be RNA, such as mRNA or hnRNA, and the like.

Those skilled in the art can easily mutate the nucleotide sequence of the present invention by using known methods, such as directed evolution and point mutation. Those artificially modified nucleotides which have a certain identity with the nucleotide sequence of the present invention, as long as encoding the antibody or the antigen-binding fragment thereof or the variant and having functions of the antibody or the antigen-binding fragment thereof or the variant, are derived from the nucleotide sequence of the present invention and are equivalent to the sequence of the present invention.

As used herein, the term "identity" refers to sequence similarity with a nucleic acid sequence. "Identity" may be evaluated with naked eyes or computer software. The identity between two or more sequences may be expressed as a percentage (%) using computer software, and may be used to evaluate the identity between related sequences.

In some embodiments, in the above biological material, the expression cassette containing the nucleic acid molecule of B1) mentioned in B2) refers to a DNA molecule that can express the antibody or the antigen-binding fragment thereof or the variant in a host cell, and the DNA molecule may comprise not only a promoter that starts transcription of a gene encoding the antibody or the antigen-binding fragment thereof or the variant, but also a terminator that stops transcription of a gene encoding the antibody or the antigen-binding fragment thereof or the variant. Further, the expression cassette may also comprise an enhancer sequence.

An existing expression vector, such as a pcDNA3.1 vector, may be used to construct a recombinant vector containing a nucleic acid molecule encoding the antibody or the antigen-binding fragment thereof or the variant. A light chain expression vector may be pcDNA3.1_CAN001 LC, and a heavy chain expression vector may be pcDNA3.1_CAN001 HC.

The vector may be a plasmid, cosmid, phage or virus vector;

the recombinant microorganism may specifically be bacteria, algae and fungi, wherein the bacteria may be *Escherichia coil*; and the recombinant cell is of a non-reproductive material.

In some embodiments, in the above biological material, the nucleic acid molecule comprises a nucleic acid fragment shown in the following 1), or 2), or 3):

(1) the following DNA molecules:

the nucleic acid fragment shown in positions 130-168 in SEQ ID NO: 1;

the nucleic acid fragment shown in positions 214-234 in SEQ ID NO: 1;

the nucleic acid fragment shown in positions 331-357 in SEQ ID NO: 1;

the nucleic acid fragment shown in positions 154-168 in SEQ ID NO: 2;

the nucleic acid fragment shown in positions 211-261 in SEQ ID NO: 2;

the nucleic acid fragment shown in positions 358-378 in SEQ ID NO: 2;

the nucleic acid fragment shown in positions 64-405 in SEQ ID NO: 1;

the nucleic acid fragment shown in positions 64-441 in SEQ ID NO: 2;

the nucleic acid fragment shown in SEQ ID NO: 1; or, the nucleic acid fragment shown in SEQ ID NO: 2;

2) a DNA molecule hybridizing to the DNA molecule defined in 1) and encoding any one of the antibodies or the antigen-binding fragments thereof mentioned above or the variants mentioned above; and 3) a DNA molecule having at least 90% identity with the DNA molecule defined in 1) or 2) and encoding any one of the antibodies or the antigen-binding fragments thereof mentioned above or the variants mentioned above.

In another aspect, the present invention further provides a method for preparing any one of the antibodies or the antigen-binding fragments thereof mentioned above or the variants mentioned above, wherein the method comprises:

culturing a recombinant cell containing the nucleic acid molecule of B1) in a culture under a condition that the nucleic acid molecule is capable of being expressed, so as to prepare the antibody or the antigen-binding fragment thereof or the variant.

In some embodiments, the light chain expression vector pcDNA3._AN001 LC and the heavy chain expression vector pcDNA3.1_CAN001 HC are transfected into HEK293T cells, the transfected HEK293T cells are cultured, and the supernatant is collected to obtain the antibody or the antigen-binding fragment thereof or the variant. Preferably, the HEK293T cells are co-transfected with vectors pcDNA3.1_CAN001 HC and pcDNA3.1_CAN001 LC (mass ratio=1:2) encoding the heavy chain and light chain of CAN001 respectively and 25 kD linear PEI polymer (polyscience) according to a mass ratio of vector to polymer of 1:3.

In some embodiments, after collection, the supernatant may be further purified to obtain the antibody or the antigen-binding fragment thereof or the variant, and the purification may be performed by protein-A affinity chromatography (Genescript).

In another aspect, the present invention further provides an antibody-drug conjugate obtained by coupling any one of the antibodies or the antigen-binding fragments thereof mentioned above or the variants mentioned above with a cytotoxic drug via a linker. The antibody-drug conjugate enables the antibody or the antigen-binding fragment thereof or the variant to target and bind to human follicle stimulating hormone receptor FSHR on the surface of a target cell, and then to be endocytosed into the target cell together with the drug.

As used herein, the term "drug" or "D" refers to a cytotoxic drug, and examples comprise chemotherapeutic agents and toxins. Particularly, "drug" may be independently selected from: (a) camptothecin derivative and metabolite (such as SN-38), wherein others comprise diphtheria toxin, botulinum toxin, tetanus toxin, dysentery toxin, cholera toxin, amanitin, 0-amanitin, amanitin derivative, pyrrolo-benzodiazepine, pyrrolo-benzodiazepine derivative, tetrodotoxin, brevetoxin, ciguatera toxin, ricin, AM toxin, tubulysin, geldanamycin, maytansinol, calicheamicin, daunorubicin, adriamycin, methotrexate, vindesine, SG2285, dolastatin, dolastatin analogue, auristatin (such as monomethyl auristatin E and monomethyl auristatin F), cryptophycin, camptothecin, rhizoxin, rhizoxin derivative, CC-1065, CC-1065 analogue or derivative, duocarmycin, enediyne antibiotic, lamycin, epothilone, azonafide, aplidine, toxoid, or any combination of them; (b) erlotinib, bortezomib, fulvestrant, sutent, letrozole, imatinib mesylate, PTK787/ZK 222584, oxaliplatin, 5-fluorouracil, folinic acid, rapamycin, lapatinib, lonafarnib, sorafenib, gefitinib, AG1478, AG1571, thiotepa, cyclophosphamide, busulfan, improsulfan, piposulfan, benzodopa, carboquone, meturedopa, uredopa, ethyleneimine, altretamine, tretamine, trietylenephosphoramide, riethiylenethiophosphoramide, trimethylolomelamine, bull atacin, bull atacinone, amptothecin, topotecan, bryostatin, callystatin, CC-1065, adozelesin, carzelesin, bizelesin, cryptophycin 1, cryptophycin 8, dolastatin, duocarmycin, KW-2189, CB1-TM1, eleutherobin, pancratistatin, sarcodictyin, spongistatin, chlorambucil, chlornaphazine, cholophosphamide, estramustine, ifosfamide, nitrogen mustard, melphalan, novembichin, phenesterine, prednimustine, trofosfamide, uramustine, carmustine, chlorozotocin, fotemustine, lomustine, nimustine, ranimustine, calicheamicin, calicheamicin γ1, calicheamicin ω1, dynemicin, dynemicin A, clodronate, lamycin, neocarzinostatin chromophore, aclacinomysins, actinomycin, antimycin, azaserine, bleomycin, actinomycin C, carabicin, carninomycin, carzinophilin, chromomycin, actinomycin D, daunomycin, detorubucin, 6-diazo-5-oxo-L-norleucine, adriamycin, morpholino-adriamycin, cyanomorpholino-adriamycin, 2-pyrrolo-adriamycin, liposome adriamycin, deoxyadriamycin, epirubicin, esorubicin, marcellomycin, mitomycin C, mycophenolic acid, nogalamycin, olivomycin, peplomycin, potfiromycin, puromycin, quelamycin, rodorubicin, streptomigrin, streptozotocin, tubercidin, ubenimex, zinostatin, zorubicin, 5-fluorouracil, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, folinic acid, aceglatone, aldophosphamide glycoside, aminolevulinic acid, eniluracil, amsacrine, bestrabucil, bisantrene, edatraxate, defofamin, demecolcine, diaziquone, elfornithine, elliptinium acetate, etoglucid, gallium nitrate, hydroxyurea, lentinan, lonidainine, maytansine, ansamitocin, mitoguazone, mitoxantrone, mopidanmol, nitraerine, pentostatin, phenamet, pirarubicin, losoxantrone, 2-ethylhydrazide, procarbazine, polysaccharide k, razoxane, rhizoxin, sizofiran, spirogermanium, tenuazonic acid, triaziquone, 2,2',2"-trichlorotriethylamine, T-2 toxin, verracurin A, myrothecin A, anguidin, urethane, vindesine, dacarbazine, mannomustine, dibromannitol, dibromodulcitol, pipobroman, gacytosine, arabinoside, cyclophosphamide, thiotepa, paclitaxel, albumin-engineered nano-preparation of paclitaxel, docetaxel, chlorambucil, gemcitabine, 6-thioguanine, mercaptopurine, cisplatin, carboplatin, vinblastine, platinum, etoposide, ifosfamide, mitoxantrone, vincristine, vinorelbine, mitoxantrone, teniposide, edatrexate, daunorubicin, aminopterin, xeloda, ibandronate, CPT-11, topoisomerase inhibitor RFS 2000, difluoromethylornithine, retinoic acid, capecitabine, or any pharmaceutically acceptable salt, solvate or acid of them; (c) an affinity ligand, wherein the affinity ligand is a substrate, an inhibitor, an irritant, a neurotransmitter, a radioisotope, or any combination of them; (d) radiolabels "P" and "S", fluorescent dye, an electron dense reagent, enzyme, biotin, streptavidin, digoxin, hapten, immunogenic protein, a nucleic acid molecule with a sequence complementary to a target, or any combination of them; (e) an immunomodulatory compound, an anticancer agent, an antiviral agent, an antibacterial agent, an antifungal agent and an antiparasitic agent, or any combination of them; (f) tamoxifen, raloxifene, droloxifene, 4-hydroxytamoxifen, trioxifene, keoxifene, LY1170 18, onapristone or toremifene; (g) 4(5)-imidazole, aminoglutethimide, megestrol acetate, exemestane, letrozole or astrazole; (h) flutamide, nilutamide, bicalutamide, leuprorelin, goserelin or troxacitabine; (i) aromatase inhibitor; (j) protein kinase inhibitor; (k) lipid kinase inhibitor; (1) antisense oligonucleotide; (m) ribozyme; (n) vaccine; (o) an antiangiogenic agent. In some embodiments, the toxin is preferably auristatin, and more preferably monomethylauristatin F (MMAF).

In some embodiments, in any one of the above antibody-drug conjugates, the linker is selected from maleimidocaproyl (mc) or an analogue thereof.

In some embodiments, in any one of the above antibody-drug conjugates, the antibody-drug conjugate has an average drug-antibody ratio (DAR) in a range of 1-30, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and an average drug-antibody ratio (DAR) between any two of the above values, such as an average drug-antibody ratio (DAR) of 5-6.

In another aspect, the present invention further provides a method for preparing any one of the antibody-drug conjugates, comprising: connecting the linker to the drug, coupling the linker-drug moiety to the antibody, and purifying the antibody-drug conjugate.

Other methods for preparing antibody-drug conjugates have been described in various publications. For example, the antibody may be chemically modified via cysteine sulfhydryl activated by reducing interchain disulfide bonds for a conjugation reaction.

In some embodiments, in the above antibody-drug conjugates, the cytotoxic drug is MC-MMAF (Maleimidocaproyl monomethylauristatin F), which is linked to an S atom of cysteine of any one of the antibodies or the antigen-binding fragments thereof mentioned above or the variants mentioned above to obtain the antibody-drug conjugate. Preferably, any one of the antibodies or the antigen-binding fragments thereof mentioned above or the variants mentioned above is reduced under the action of TCEP (tris(2-carboxyethyl)phosphine) to expose the S atom of cysteine, and then the drug linker MC-MMAF is connected to the S atom to realize coupling, and the product is purified by illustra NAP-10 column (GE Healthcare).

In another aspect, the present invention further provides a pharmaceutical composition, comprising any one of the antibodies or the antigen-binding fragments thereof mentioned above or the variants mentioned above or any one of the antibody-drug conjugates mentioned above, and a pharmaceutically acceptable carrier.

In another aspect, the present invention further provides use of any one of the antibodies or the antigen-binding fragments thereof mentioned above or the variants mentioned above or any one of the antibody-drug conjugates mentioned above in preparing any one of the following products:

(1) a product for detecting expression of human follicle-stimulating hormone receptor; and (2) a product for detecting, screening, preventing and/or treating a cancer.

In some embodiments, in the above use, the cancer is prostate cancer, breast cancer, colon cancer, pancreatic cancer, bladder cancer, kidney cancer, lung cancer, liver cancer, stomach cancer, testicular cancer or ovarian cancer.

In another aspect, the present invention further provides a kit, comprising any one of the antibodies or the antigen-binding fragments thereof mentioned above or the variants mentioned above or any one of the antibody-drug conjugates mentioned above.

In another aspect, the present invention further provides a method for inhibiting growth of a cancer cell, comprising contacting the cell with any one of the antibody-drug conjugates mentioned above.

In some embodiments, the cancer cell is a prostate cancer cell, a breast cancer cell, a colon cancer cell, a pancreatic cancer cell, a bladder cancer cell, a kidney cancer cell, a lung cancer cell, a liver cancer cell, a gastric cancer cell, a testicular cancer cell or an ovarian cancer cell.

In another aspect, the present invention further provides a method for treating a cancer patient, comprising administering a therapeutically effective amount of any one of the antibody-drug conjugates mentioned above to the patient.

In some embodiments, in the above method, the cancer is prostate cancer, breast cancer, colon cancer, pancreatic cancer, bladder cancer, kidney cancer, lung cancer, liver cancer, stomach cancer, testicular cancer or ovarian cancer.

In some embodiments, any one of the methods above further comprises administering an additional therapeutic agent to the patient. Suitable therapeutic agents comprise existing drugs and/or surgical treatments for specific uses such as cancer. For example, the antibody-drug conjugate is used in combination with one or more other chemotherapeutic or antitumor agents. Alternatively, the other therapeutic agent is radiotherapy.

In some embodiments, the therapeutic agent is a cytotoxic agent.

In another aspect, the present invention further provides a method for diagnosing a subject suspected of suffering from a cancer, wherein the method comprises administering to the subject any one of the antibodies or the antigen-binding fragments thereof mentioned above or the variants mentioned above linked with a detectable label, and detecting distribution of the labeled antibody or the antigen-binding fragment thereof or the variant in the subject.

It should be understood by those skilled in the art that the antibody or the antigen-binding fragment thereof or the variant or the antibody-drug conjugate of the present invention has various uses, for example, the antibody-drug conjugate of the present invention may be used as a therapeutic agent, the antibody or the antigen-binding fragment thereof or the variant of the present invention may used as a reagent in a diagnostic kit or as a diagnostic tool.

The anti-FSHR antibody, CAN001, provided by the present invention can specifically binds to FSHR, and the CAN001 antibody-drug conjugate, CAN001-MC-MMAF, obtained on the basis of the anti-FSHR antibody can obviously kill cancer cells. The anti-FSHR antibody and the antibody-drug conjugate thereof provided by the present invention have broad application prospects in detecting, screening, and treating cancers.

DETAILED DESCRIPTION OF THE INVENTION

Figure 1:
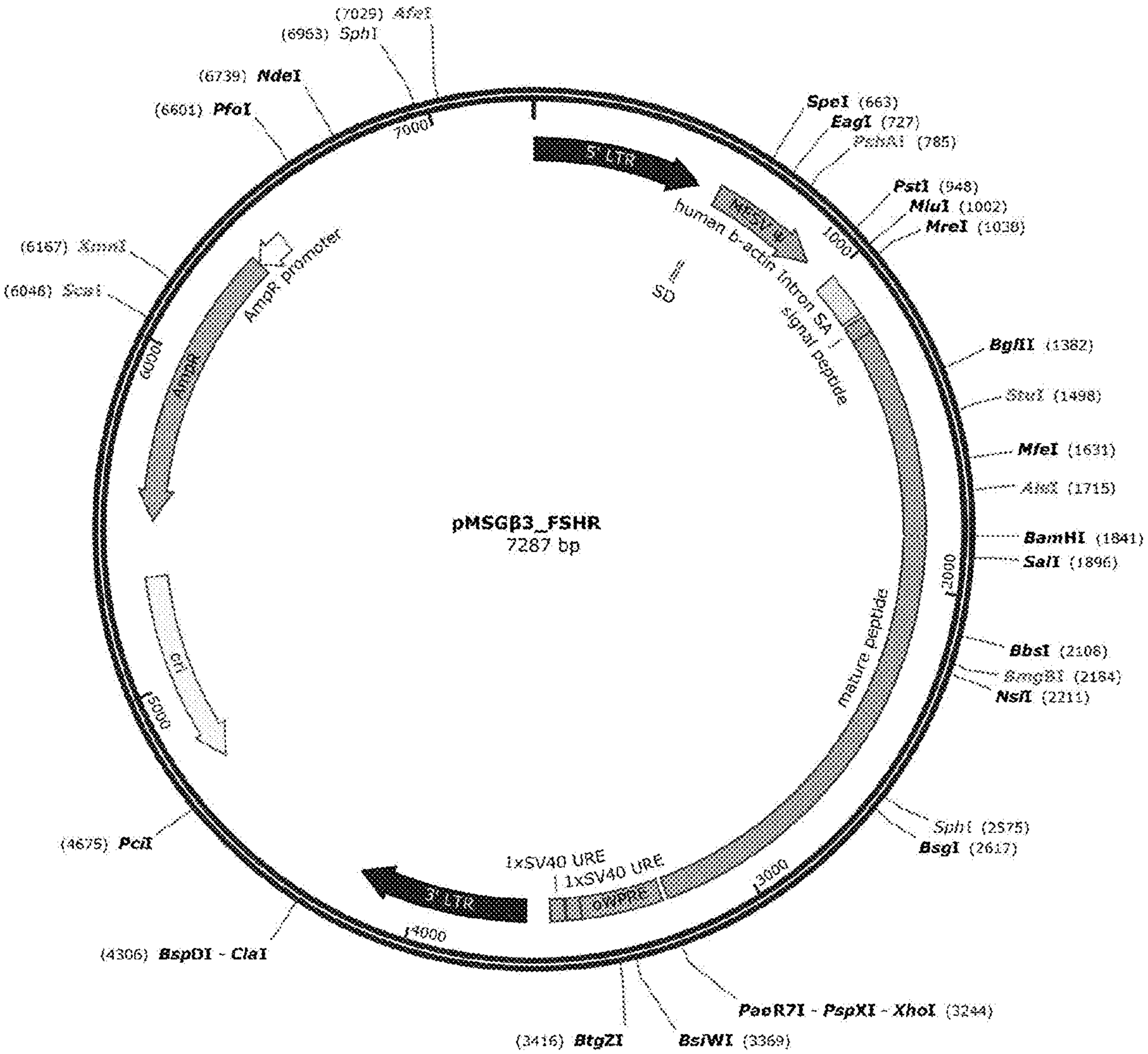
FIG. 1 shows a plasmid map of pMSG133

The present invention is described hereinafter with reference to particular specific embodiments, and those skilled in the art may easily understand the advantages and effects of the present invention from the contents disclosed in the specification. The present invention may also be implemented or applied by other different specific embodiments, and various details in the specification may also be modified or changed without departing from the spirit of the present invention based on different viewpoints and applications. It should be understood that the protection scope of the present invention is not limited to the following specific embodiments. It should also be understood that the terms used in the embodiments of the present invention are for the purpose of describing the particular specific embodiments instead of limiting the protection scope of the present invention.

Where a numerical range is given in examples, it should be understood that unless otherwise specified in the present invention, any numerical value at two endpoints of each numerical range and between the two endpoints can be selected. Unless otherwise defined, all technical and scientific terms used in the present invention have the same meanings as those commonly understood by those skilled in the art. In addition to the specific methods, devices and materials used in the examples, according to the mastery of the prior art by those skilled in the art and the records of the present invention, any methods, devices and materials in the prior art similar to or equivalent to the methods, devices and materials described in the examples of the present invention may be used to realize the present invention.

Unless otherwise specified, the experimental methods, detection methods and preparation methods disclosed in the present invention all adopt conventional technologies in molecular biology, biochemistry, chromatin structure and analysis, analytical chemistry, cell culture, recombinant DNA technology and related fields. These technologies have been well described in existing literatures, and may specifically refer to Sambrook, et al. MOLECULAR CLONING: A LABORATORY MANUAL, Second Edition, Cold Spring Harbor Laboratory Press, 1989 and Third edition, 2001; Ausubel, et al., CURRENT PROTOCOLS IN MOLECULAR BIOLOGY, John Wiley&Sons, New York, 1987 and periodic updates: the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, Chromatin (P. M. Wassarman and A. P. Wolffe, eds.), Academic Press, San Diego, 1999; and METHODS IN MOLECULAR BIOLOGY, Vol. 119, Chromatin Protocols (P. B. Becker, ed.), Humana Press, Totowa, 1999, etc.

The term "antibody" used herein refers to an immunoglobulin (Ig) molecule and an immunocompetent part of an immunoglobulin molecule, which is namely a molecule containing an antigen-binding site with specific binding to an antigen (and immunoreaction with the antigen). "Specific binding" or "immunoreaction" or "targeting" means that the antibody reacts with one or more antigenic determinants of a target antigen and does not react with other polypeptides, or binds to other polypeptides with very low affinity ($Kd>10^{-6}$ g/ml). The antibody comprises, but is not limited to, a monoclonal antibody, a chimeric antibody, a dAb (domain antibody), a single chain antibody, Fab, Fab' and F (ab') 2 fragments, and Fv and Fab expression libraries.

It is known that a basic antibody structural unit comprises a tetramer. Each tetramer (or "complete antibody") consists of two pairs of identical polypeptide chains, and each pair comprises a "light" chain and a "heavy" chain. The amino terminal part of each chain comprises a variable region of about 100 to 110 or more amino acids, which is mainly responsible for antigen recognition. The carboxyl terminal part of each chain defines a constant region, which is mainly responsible for an effector function. Generally speaking, the antibody molecule obtained from human body involves any class of IgG, IgM, IgA, IgE and IgD, which are different from each other due to the nature of the heavy chain in the molecule. These classes also have subclasses, such as IgG1, IgG2 and others. In addition, the light chain may be a κ chain or a λ chain in human body.

As used herein, the term "monoclonal antibody" (mAb) refers to a group of antibody molecules that contain only one molecular class of antibody molecules consisting of a unique light chain gene product and a unique heavy chain gene product. Specifically, the complementarity determining regions (CDRs) of monoclonal antibodies are identical among all molecules of the population. The mAb contains the antigen-binding site capable of reacting with a specific epitope of the antigen.

As used herein, the term "specific binding" refers to a type of noncovalent interaction occurring between the immunoglobulin molecule and the antigen for which the immunoglobulin is specific. The intensity or affinity of immunological binding interaction may be expressed by a dissociation constant (Kd) of the interaction, wherein a smaller Kd represents a greater affinity. The immunobinding property of a selected polypeptide may be quantified by methods well known in the art.

As used herein, the terms "complementarity determining region" and "CDR" are intended to refer to discontinuous antigen binding sites found in variable regions of HC and LC polypeptides of an antibody. These specific regions have been described by others, including Kabat, et al., *Ann. NY Acad. Sci.* 190:382-93(1971); Kabat, et al., *J. Biol. Chem.* 252:6609-6616(1977); Kabat, et al., Sequences of Proteins of Immunological Interest, Fifth edition, U.S. Department of Health and Human Services, NIH Publication No. 91-3242 (1991); Chothia, et al., *J. Mol. Biol.* 196:901-917(1987); MacCallum, et al., *J. Mol. Biol.,* 262:732-745(1996); and North, et al., *J. Mol. Biol.,* 406, 228-256(2011), wherein the definition comprises the overlap or subgroup of amino acid residues when the regions are compared with each other.

The CDRs are interspersed in a more conservative region, which is called a frame region ("FR"). Each LCVR or HCVR consists of three CDRs and four FRs, which are arranged from an amino terminal to a carboxyl terminal in the following order: FR1, CDR1, FR2, CDR2, FR3, CDR3 and FR4. The three CDRs of the light chain are called "LCDR1, LCDR2 and LCDR3", and the three CDRs of the heavy chain are called "HCDR1, HCDR2 and HCDR3". The CDRs contains most residues forming specific interaction with the antigen. The numbering and positioning of the amino acid residues of the CDRs in the LCVR and HCVR regions in the present invention are defined according to the Kabat numbering scheme.

An "isolated" antibody is an antibody isolated and/or recovered from a component of its natural environment. A polluting component of its natural environment is a substance that would interfere with the diagnostic or therapeutic use of the antibody, and may include an enzyme, a hormone, and other protein or non-protein solutes. In some solutions, the antibody is purified to the following extent: (1) the antibody is greater than 95% by weight, such as greater than 99%, as determined by the Lowry method; (2) at least 15 residues of an N-terminal or an internal amino acid sequence may be obtained by a spinning cup sequencer; or (3) the homogeneity is detected by Coomassie blue or silver staining through SDS-PAGE under a reduced or non-reduced condition. The isolated antibody includes an in-situ antibody in a recombinant cell. Generally, the isolated antibody will be prepared by at least one or more purification steps. In some embodiments, the purity of the isolated antibody is at least about 50%, about 60%, about 70%, about 80%, about 90%, about 95%, about 99%, or a range between any two of these values (inclusive) or any value in the range.

The term "sequence identity" means that two polynucleotide or amino acid sequences are identical (i.e., on a nucleotide-by-nucleotide basis or a residue-by-residue basis) over the window of comparison. The term "percentage of sequence identity" is calculated by comparing two optimally aligned sequences over the window of comparison, determining the number of positions at which the identical nucleic acid base (e.g., A, T, C, G, or U) or amino acid residue occurs in both sequences to yield the number of matched positions, dividing the number of matched positions by the total number of positions in the window of comparison (i.e., the window size), and multiplying the result by 100 to yield the percentage of sequence identity.

Minor changes in the amino acid sequence of the antibody or the immunoglobulin molecule are all encompassed by the present disclosure, provided that the identity of the amino acid sequence remains at least 75%, such as at least 80%, 90%, 95% and 99%. In some embodiments, the change is a conservative amino acid substitution. The conservative amino acid substitution is a substitution in a amino acid family in which side chains are related. Gene-encoded amino acids are approximately divided into the following categories: (1) acidic amino acids: aspartate and glutamate; (2) basic amino acids: lysine, arginine and histidine; (3) nonpolar amino acids: alanine, valine, leucine, isoleucine, proline, phenylalanine, methionine and tryptophan; and (4) uncharged polar amino acids: glycine, asparagine, glutamine, cysteine, serine, threonine and tyrosine. Amino acids of other families comprise (i) serine and threonine of the aliphatic-hydroxyl family; (ii) asparagine and glutamine of the amide-containing family; (iii) alanine, valine, leucine and isoleucine of the aliphatic family; and (iv) phenylalanine, tryptophan and tyrosine of the aromatic family. In some embodiments, conservative amino acid substitution groups are: valine-leucine-isoleucine, phenylalanine-tyrosine, lysine-arginine, alanine-valine, glutamic acid-aspartic acid and asparagine-glutamine. For example, it can be reasonably predicted that when leucine is substituted by isoleucine or valine alone, aspartate is substituted by glutamate, threonine is substituted by serine, or one amino acid is similarly substituted by a structurally related amino acid, the binding or characteristics of the obtained molecule will not be significantly affected, particularly when the substitution does not involve the amino acid in the binding site. Whether the change of the amino acid produces a functional peptide may be easily determined by measuring the specific activity of a polypeptide derivative. The determination is described in detail herein. A fragment or an analogue of the antibody or the immunoglobulin molecule may be easily prepared by those of ordinary skills in the art.

The term "pharmaceutically acceptable" refers to a component suitable for being applied to human and/or animal without excessive adverse side effects (such as toxicity, irritation and allergic reaction) commensurate with a reasonable benefit/risk ratio.

The term "carrier" refers to a diluent, an adjuvant, an excipient or a carrier used with an active ingredient for treatment. Such drug carrier can be a sterile liquid, such as water and oil, including oil from petroleum, animals and plants, or synthetic sources, such as peanut oil, soybean oil, mineral oil and sesame oil. In some embodiments, when a pharmaceutical composition is administered intravenously, the carrier can be water. A saline solution, a glucose aqueous solution and a glycerol aqueous solution may also be used as liquid carriers, especially for injection solutions. Examples of suitable pharmaceutical carriers are described in E. W. Martin, et al. Remington's Pharmaceutical Sciences, which is incorporated herein by reference. Such compositions will comprise a clinically effective dose of antibody or antibody fragment, together with suitable carriers, to provide an administration form suitable for patients. The preparation should be suitable for the administration mode. The preparation may be packaged in an ampoule bottle, a disposable syringe or a multi-dose vial made of glass or plastic.

The term "gene" is used for referring to a coding unit for a functional protein, a polypeptide or a peptide. As understood by those skilled in the art, this functional term comprises a genome sequence, a cDNA sequence, or a fragment or combination thereof, and a gene product, including a gene product that may have been artificially changed. Purified genes, nucleic acids, proteins and analogues are those identified entities that have been recognized and isolated from at least one contaminating nucleic acid or protein usually associated with them.

As used herein, the term "sequence" is used for referring to a nucleotide or an amino acid sequence, whether natural or artificial, such as a modified nucleic acid or amino acid sequence.

In some embodiments, the substitution of amino acid has the following effects: (1) the sensitivity to proteolysis is reduced, (2) the sensitivity to oxidation is reduced, (3) the binding affinity for forming a protein complex is changed, (4) the binding affinity is changed, and (5) other physicochemical or functional characteristics of such analogues are endowed or improved. The analogues may comprise various mutant proteins with sequences different from natural peptide sequences. For example, single or multiple amino acid substitutions (preferably conservative amino acid substitution) may be performed in natural sequences (preferably in a polypeptide part beyond a structural domain forming intermolecular contact). The conservative amino acid substitution should not significantly change structural characteristics of a parent sequence (for example, the substituted amino acid should not tend to destroy a helical structure in the parent sequence or other types of secondary structures characterizing the parent sequence). Examples of secondary and tertiary structures of an artificially identified polypeptide are described in Proteins, Structures and Molecular Principles (edited by Creighton, W. H. Freeman and Company, New York (1984)); Introduction to Protein Structure (edited by C. Branden and J. Tooze, Garland Publishing, New York, N.Y. (1991)); and Thornton, et al., Nature 354:105 (1991).

The antibody may be purified by a well-known technology, such as affinity chromatography using protein A or protein G, which mainly provides the IgG fraction in immune serum. In addition, the specific antigen targeted by the immunoglobulin or an epitope thereof may be immobilized on a column to purify an immunospecific antibody by immunoaffinity chromatography. The purification of immunoglobulins may refer to the literature of D. Wilkinson. (The Scientist, published by The Scientist, Inc., Philadelphia Pa., Vol. 14, No. 8 (Apr. 17, 2000), Pages 25-28).

As used herein, the term “pharmaceutically acceptable carrier” is intended to comprise any and all solvents, stabilizers, buffers, dispersion media, coatings, bacteriostats, isotonic agents, absorption retardants and the like that are compatible with drug administration. Suitable carriers are described in the latest edition of Remington’s Pharmaceutical Sciences. Such carriers or diluents may optionally include, but are not limited to, water, saline, a Ringer’s solution, a glucose solution and 5% human serum albumin.

When referring to animals, humans, subjects, cells, tissues, organs or biological fluids, “administration” and “treatment” mean that exogenous drugs, therapeutic agents, diagnostic agents or compositions are brought into contact with animals, humans, subjects, cells, tissues, organs or biological fluids. “Administration” and “treatment” may refer to, e.g., a therapeutic method, a pharmacokinetic method, a diagnostic method, a research method and an experimental method. Cell treatment comprises contacting a reagent with cells and contacting the reagent with a fluid, wherein the fluid is contacted with the cells. “Administration” and “treatment” also refer to in-vitro and ex-vivo treatments of cells e.g., by a reagent, a diagnostic agent, a binding composition or other cells.

As used herein, “inhibition” or “treatment” comprises delaying the development of symptoms associated with a disease and/or reducing the severity of these symptoms that the disease will or is expected to develop. The term further comprises alleviating existing symptoms, preventing other symptoms, and alleviating or preventing potential causes of these symptoms. Therefore, the term indicates that beneficial results have been given to a vertebrate subject suffering from the disease, such as a human.

As used herein, the term “therapeutically effective amount” or “effective amount” refers to an amount capable of effectively preventing or alleviating a disease or condition to be treated when an antibody-drug conjugate is administered alone or in combination with another therapeutic agent to cells, tissues or subjects. The therapeutically effective amount further refers to an amount of the antibody-drug conjugate sufficient to realize symptom alleviation, and the symptom alleviation refers to, e.g., treatment, curing, prevention or alleviation of related medical conditions, or improvement of treatment rate, cure rate, prevention rate or alleviation rate of the symptoms. An effective amount for a specific subject may vary depending on many factors, such as a disease to be treated, the general health of the patient, the administration route and dose, and the severity of side effects. The effective amount may be a maximum dose or an administration regimen capable of avoiding significant side effects or toxic effects. When an active ingredient is administered alone to an individual, the therapeutically effective amount refers to the amount of that ingredient alone. When a combination is administered, the therapeutically effective amount refers to a combined dose of the active ingredients producing a therapeutic effect, regardless of whether the active ingredients are administered jointly, continuously or simultaneously. The therapeutically effective amount will generally alleviate the symptoms by at least 10%, usually by at least 20%, preferably by at least about 30%, more preferably by at least 40% and most preferably by at least 50%.

Monoclonal Antibodies

Monoclonal antibodies against FSHR can be prepared according to the knowledge and skills in the art.

The DNA sequences (such as the light chain DNA sequence and the heavy chain DNA sequence) of the monoclonal antibody can be easily synthesized by a conventional method, the DNA sequences can be placed in expression vectors (such as a light chain expression vector and a heavy chain expression vector constructed), and these vectors are then transfected into host cells (e.g., such as HEK293T cells, CHO cells, NSO cells or myeloma cells that do not produce other immunoglobulins) to synthesize the monoclonal antibody in recombinant host cells. The recombinant preparation of antibodies will be described in more detail below.

Antibody-Drug Conjugates

The monoclonal antibody of FSHR may be coupled with a drug linker (such as MC-MMAF), which is usually linked to the S atom of cysteine of the antibody.

Therapeutic Uses of Antibodies and Antibody-Drug Conjugates of the Present Invention The antibodies or the antigen-binding fragments or the antibody-drug conjugates of the present invention specifically binding to FSHR can be used for specifically recognizing cells and tissues expressing FSHR.

In some embodiments, the present invention further provides a method for treating a disease. The method comprises administering a therapeutically effective amount of the antibody-drug conjugate of the present invention to a patient in need thereof. In some embodiments, the disease is a cancer.

Cancers

The antibody-drug conjugates of the present invention can be used for treating a cancer (i.e., inhibiting the growth or survival of tumor cells). In some embodiments, the cancers with growth inhibited by the antibody-drug conjugates of the present invention typically include prostate cancer, breast cancer, colon cancer, pancreatic cancer, bladder cancer, kidney cancer, lung cancer, liver cancer, stomach cancer, testicular cancer and ovarian cancer.

Non-Therapeutic Uses of Antibodies and Antibody-Drug Conjugates of the Present Invention The antibodies and the antibody-drug conjugates of the present invention can be used for diagnosis, such as for detecting the expression of FSHR in specific cells, tissues or serums. For diagnostic use, the antibodies are usually labeled (directly or indirectly) with a detectable part. Numerous labels can be used, which are generally divided into the following categories: biotin, fluorescent dyes, radioactive nucleotides, enzymes, iodine and biosynthetic labels.

The antibodies of the present invention can also be used for in-vivo diagnosis. The antibodies are usually labeled with a radionuclide (such as $^{111}I$, $^{99}Tc$, $^{4}C$, $^{125}I$, $^{3}H$, $^{32}P$, $^{35}S$ or $^{18}F$), so that the antigen or the cell expressing the antibody can be located by immunoscintigraphy or positron imaging.

Pharmaceutical Compositions

The present invention further provides pharmaceutical compositions. The composition comprises an effective amount of the antibody-drug conjugate and a pharmaceutically acceptable carrier.

In some embodiments, the term "pharmaceutically acceptable carrier" refers to a substance used in animals (especially in human beings) approved by government regulatory agencies or listed in other recognized pharmacopoeias. In addition, the "pharmaceutically acceptable carrier" can generally be any type of non-toxic solid, semi-solid or liquid filler, diluent, encapsulating material or preparation adjuvant.

Example 1: Mouse Anti-Human FSHR Monoclonal Antibody CAN001

1. The codon-optimized DNA fragments (shown in SEQ ID NO: 1 and SEQ ID NO: 2 respectively) that encode the light chain and the heavy chain of an anti-human FSHR monoclonal antibody were synthesized by Genescript, and nucleotide sequences of synthesized DNA fragments were sequence validated.

```
SEQ ID NO: 1: Light chain DNA sequence
ATGGCCCTCCCTGTCACCGCCCTGCTGCTTCCGCTGGCTCTTCTGCTCCA

CGCCGCTCGGCCCCAGATAGTACTTACGCAATCACCCGTCATAATGAGCG

CATCCCCTGGTGAAAAGGTTACTCTGACATGCTCTGCGTCTTCCAGCGTG

AGTAGTTCTTATCTCTATTGGTATCAGCAAAAACCCGGATCTTCTAGTAA

ATTGTGGATATATTCTACGTCTAATCTTGCGTCAGGAGTGCCTGCTCGGT

TTTCTGGGTCCGGGTCCGGGACCAGCTATAGTTTGACTATAAGTAGTATG

GAGGCGGAGGACGCAGCTAGCTACTTTTGCCATCAATGGAGCTCCTATCC

TCCTACCTTTGGGGGCGGAACCAAATTGGAAATCAAAAGAGCCGACGCGG

CACCCACTGTATCTATCTTCCCACCCTCATCAGAACAGCTCACTTCAGGC

GGCGCCAGTGTGGTGTGTTTCCTCAACAACTTCTATCCTAAAGACATAAA

TGTAAAATGGAAAATAGACGGTAGCGAGCGGCAAAACGGGGTGCTGAACT

CATGGACGGACCAAGATTCCAAGGATTCTACCTATTCAATGAGTTCTACA

TTGACACTTACGAAAGACGAATACGAGCGCCACAATTCCTATACGTGCGA

AGCAACGCACAAAACCTCCACTTCCCCGATTGTGAAGTCCTTCAATAGGA

ATGAATGTTGATAA
```

The DNA sequence of the light chain variable region is shown in positions 64-405 in SEQ ID NO: 1, the DNA sequence of the light chain CDR1 is shown in positions 130-168, the DNA sequence of the light chain CDR2 is shown in positions 214-234, and the DNA sequence of the light chain CDR3 is shown in positions 331-357.

```
SEQ ID NO: 2: Heavy chain DNA sequence
ATGGAGTTTGGGCTCAGTTGGGTCTTTCTCGTGGCACTGTTTCGCGGGGT

ACAGTGCGCTAGCCAAGTACAACTGCAACAACCAGGCGCGGAGCTCGTTA

AACCGGGGGCGAGCGTCAACCTTAGCTGCAAAGCCTCCGGTTATACCTTT

ACAAGTTACTGGATGCACTGGGTGAAGCAGCGACCAGGGCAAGGACGCGA

ATGGATCGGGGAAATAAATCCAAGGAACGGCAGAACGAATTACAACGAGA
```

-continued

```
AGTTCAAATCCAAGGCGACGTTGACGGTGGACAAATCCTCTTCAACTGCT

TATATGCAGCTCAGTTCTCTGACAAGCGAGGATAGTGCCGTGTACTGTTG

CGCCAGGTTGTCTGTGGGGTTCGCCTACTGGGGGCAGGGCACGCTCGTTA

CAGTCTCTGCGGCCAAGACGACTGCGCCTTCAGTATATCCACTGGCTCCG

GTGTGCGGAGATACGACAGGTAGTTCTGTAACTTTGGGATGCCTCGTTAA

GGGTTATTTCCCGGAGCCGGTCACCTTGACGTGGAACTCCGGATCACTCT

CCTCAGGGGTACATACATTTCCAGCGGTTTTGCAGAGCGACCTCTACACA

CTCAGTAGCAGTGTAACCGTTACCTCATCCACATGGCCTAGCCAGAGTAT

CACGTGCAATGTTGCACACCCGGCAAGTTCTACCAAGGTGGACAAAAAAC

TCGAGCCTAGAGGACCGACGATAAAGCCCTGTCCGCCTTGCAAATGTCCG

GCACCTAACGCTGCTGGTGGCCCCTCTGTTTTTATATTTCCGCCAAAAAT

TAAGGACGTCCTCATGATCAGTCTGAGCCCTATAGTCACGTGTGTGGTGG

TAGATGTCTCTGAAGACGATCCCGACGTACAGATTTCATGGTTCGTGAAC

AATGTGGAGGTTCACACAGCCCAAACACAGACACACCGCGAAGATTACAA

TAGTACACTGCGGGTAGTCTCTGCCCTCCCAATACAACACCAGGACTGGA

TGAGCGGGAAAGAGTTCAAGTGCAAAGTCAATAACAAAGACCTGGGAGCG

CCGATAGAAAGAACTATAAGTAAACCAAAGGGGAGCGTAAGAGCGCCCCA

AGTGTATGTCCTCCCTCCTCCCGAAGAGGAAATGACCAAGAAACAAGTTA

CTCTCACATGCATGGTAACCGATTTCATGCCTGAAGACATATACGTAGAG

TGGACCAACAACGGGAAGACAGAATTGAACTACAAGAATACAGAGCCCGT

TCTCGATTCTGATGGCTCCTACTTTATGTATAGCAAACTCCGGGTGGAAA

AAAAGAATTGGGTCGAAAGAAACAGTTATTCATGTTCTGTTGTTCACGAG

GGTTTGCATAACCATCATACGACGAAATCTTTTTCCAGAACCCCAGGAAA

ATGA
```

The DNA sequence of the heavy chain variable region is shown in positions 64-441 in SEQ ID NO: 2, the DNA sequence of the heavy chain CDR1 is shown in positions 154-168, the DNA sequence of the heavy chain CDR2 is shown in positions 211-261, and the DNA sequence of the heavy chain CDR3 is shown in positions 358-378.

2. The DNA sequence of the light chain was cloned into pcDNA3.1 (Thermo Fisher) between Hind III site and EcoR I site by In-Fusion cloning method to create a light chain expression vector pcDNA3.1_CAN001 LC.
3. The DNA sequence of the heavy chain was cloned into pcDNA3.1 between Hind III site and EcoR I site by In-Fusion cloning method to create a heavy chain expression vector pcDNA3.1_CAN001 HC.

```
SEQ ID NO: 3: Light chain amino acid sequence
MALPVTALLLPLALLLHAARPQIVLTQSPVIMSASPGEKVTLTCSASSSV

SSSYLYWYQQKPGSSSKLWIYSTSNLASGVPARFSGSGSGTSYSLTISSM

EAEDAASYFCHQWSSYPPTFGGGTKLEIKRADAAPTVSIFPPSSEQLTSG

GASVVCFLNNFYPKDINVKWKIDGSERQNGVLNSWTDQDSKDSTYSMSST

LTLTKDEYERHNSYTCEATHKTSTSPIVKSFNRNEC
```

Based on the Kabat numbering system, the amino acid sequence of the light chain variable region is shown in positions 22-135 (SEQ ID NO: 5) in SEQ ID NO: 3, the amino acid sequence of the light chain CDR1 is shown in positions 44-56 (CSASSSVSSSYLY (SEQ ID NO: 6)), the amino acid sequence of the light chain CDR2 is shown in positions 72-78 (STSNLAS (SEQ ID NO: 7)), and the amino acid sequence of the light chain CDR3 is shown in positions 111-119 (HQWSSYPPT (SEQ ID NO: 8)).

```
SEQ ID NO: 4: Heavy chain amino acid sequence
MEFGLSWVFLVALFRGVQCASQVQLQQPGAELVKPGASVNLSCKASGYTF

TSYWMHWVKQRPGQGREWIGEINPRNGRTNYNEKFKSKATLTVDKSSSTA

YMQLSSLTSEDSAVYCCARLSVGFAYWGQGTLVTVSAAKTTAPSVYPLAP

VCGDTTGSSVTLGCLVKGYFPEPVTLTWNSGSLSSGVHTFPAVLQSDLYT

LSSSVTVTSSTWPSQSITCNVAHPASSTKVDKKLEPRGPTIKPCPPCKCP

APNAAGGPSVFIFPPKIKDVLMISLSPIVTCVVVDVSEDDPDVQISWFVN

NVEVHTAQTQTHREDYNSTLRVVSALPIQHQDWMSGKEFKCKVNNKDLGA

PIERTISKPKGSVRAPQVYVLPPPEEEMTKKQVTLTCMVTDFMPEDIYVE

WTNNGKTELNYKNTEPVLDSDGSYFMYSKLRVEKKNWVERNSYSCSVVHE

GLHNHHTTKSFSRTPGK
```

Based on the the Kabat numbering system, the amino acid sequence of the heavy chain variable region is shown in positions 22-147 (SEQ ID NO: 9) in SEQ ID NO: 4, the amino acid sequence of the heavy chain CDR1 is shown in positions 52-56 (SYWMH (SEQ ID NO: 10)), the amino acid sequence of the heavy chain CDR2 is shown in positions 71-87 (EINPRNGRTNYNEKFKS (SEQ ID NO: 11)), and the amino acid sequence of the heavy chain CDR3 is shown in positions 120-126 (LSVGFAY (SEQ ID NO: 12)).

Example 2: Cloning of Human FSHR Gene and Construction of Expression Vector

The RNA isolated from OVCAR3 cell line (ATCC, Cat. No. htb-161) was reverse transcribed into cDNA, and a fragment containing the FSHR gene was obtained by PCR with the cDNA as a template and FSHR-F and FSHR-R as primers.

```
FSHR-F:
                                    (SEQ ID NO: 13)
5'-gtttCCACAACCatggccctgctcctgg-3';
and

FSHR-R:
                                    (SEQ ID NO: 14)
5'-ggttgattaactcgagttagttttgggctaaatgacttagagggaca
ag-3'.
```

The fragment containing the FSHR gene was cloned into the cloning vector pJET2.1 (Thermo Fisher, Cat. No. 50501) to create pJET2.1-FSHR plasmid. After sequencing validation, the inserted fragment was subcloned into pMSGβ3 between Nco I and Xho I sites to create pMSGβ3_FSHR plasmid. The map of the pMSGβ3_FSHR plasmid is shown in FIG. 1.

Example 3: Production of CAN001 Antibody in HEK293T Cells

To prepare CAN001 antibody, HEK293T cells were cultured in serum free media and co-transfected with plasmid vectors pcDNA3.1_CAN001 HC and pcDNA3.1_CAN001 LC (mass ratio=1:2) encoding the heavy chain and the light chain of CAN001 respectively and 25 kD linear PEI polymer (polyscience) according to a mass ratio of vector to polymer of 1:3. HEK293T cells were cultured for 72 hours after transfection and the culture supernatant containing CAN001 antibody was collected.

Example 4: Flow Cytometry Analysis of CAN001 Antibody

Figure 2:
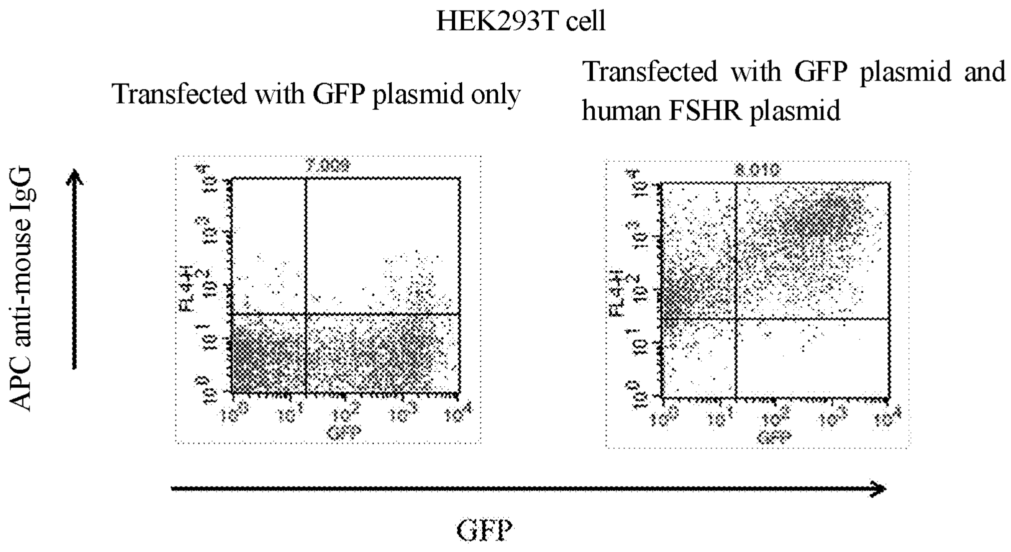
FIG. 2 shows a supernatant containing CAN001 antibody specifically staining FHSR-expressing cells but not GFP-expressing cells.

HEK293T cells were transfected with pMSGβ3_FSHR plasmid to obtain HEK293T cells expressing FSHR as the experimental group. HEK293T cells were transfected with pmaxGFP(Lonza) to obtain HEK293T cells expressing GFP protein as the negative control. After incubation with the supernatant containing the CAN001 antibody obtained in Example 3, the cells of the experimental group and negative control were stained with the CAN001 antibody and then the cells were washed and incubated with APC conjugated goat anti-mouse IgG secondary antibody. Flow cytometry was done with BD calibur and analyzed with Cellquest software. The results are shown in FIG. 2, and the results show that the supernatant containing CAN001 antibody specifically stained FHSR-expressing cells but not GFP-expressing cells.

Figure 3:
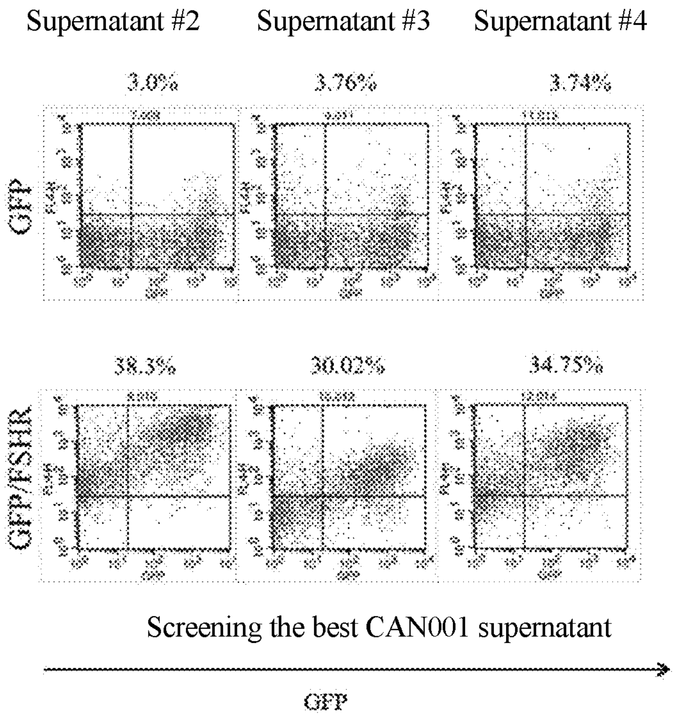
FIG. 3 shows screening for the best CAN001 supernatant.

In order to further screen the best CAN001 supernatant, HEK293T cells were co-transfected with a mixture of plasmids pcDNA3.1_CAN001 HC and pcDNA3.1_CAN001 LC with different proportions (mass ratios of pcDNA3.1_CAN001 HC to pcDNA3.1_CAN001 LC from left to right in FIG. 3 were 1:2, 1:1 and 1:3 respectively) and 25 kD linear PEI polymer according to a mass ratio of vector to polymer of 1:3. Seventy-two hours after transfection, the supernatant was collected and used to stain HEK293T cells expressing FSHR, and HEK293T cells expressing GFP protein were used as the negative control. The steps were as described above. The results of the flow cytometry analysis are shown in FIG. 3. The results show that when the mass ratio of pcDNA3.1_CAN001 HC to pcDNA3.1_CAN001 LC was 1:2, the positive stained rate of the HEK293T cells was the highest (38.3%), while when the mass ratios of pcDNA3.1_CAN001 HC to pcDNA3.1_CAN001 LC were 1:1 and 1:3, the positive stained rates of the HEK293T cells were 30.02% and 34.75% respectively. The mass ratio of pcDNA3.1_CAN001 HC to pcDNA3.1_CAN001 LC of 1:2 was selected to prepare the supernatant containing CAN001 antibody.

Example 5: IHC Staining of Human Placenta and Tumor Tissue with CAN001 Antibody Experimental Reagents:

PBS buffer (pH 7.4): 1,000 ml distilled water, 8.0 g NaCl, 0.2 g KCl, 1.149 g $Na_2HPO_4$, and 0.2 g $NaH_2PO_4$.

0.01 M citric acid buffer (pH 6.0):

Solutoin A: 29.41 g trisodium citrate-$2H_2O$+1,000 ml distilled water

Solution B: 21 g citric acid+1,000 ml distilled water

Preparation of antigen retrieval working solution: 82 ml solution A+18 ml solution B+900 ml distilled water Hematoxylin staining solution (which was stored away from light, and could be oxidized by light): the ratio was according to the instructions of the hematoxylin kit (FUZHOU MAIXIN BIOTECH, LTD., Cat. No. CTS1097), and the ratio could also be adjusted according to the test results obtained in a pre-experiment to achieve the best staining. The ratio was usually as follows: 1 ml hematoxylin stock solution+4 ml distilled water.

Gtvision III anti-mouse/rabbit universal immunohistochemical detection kit purchased from GeneTech (Shanghai) Company Limited, Cat. No. GK500705, including solution A (secondary antibody working solution): HRP labeled polymer (anti-mous, rabbit); solution B: DAB diluent buffer; and solution C: DAB stock solution. Preparation of DAB chromogenic solution: 1 ml solution B+20 μl solution C. Color development result: brown. This kit contained no avidin and streptavidin, and was not interfered by endogenous biotin.

Experimental Procedure:

1) Dewaxing and Hydration

Paraffin-embedded slides of human placenta or ovarian cancer tissue were baked in a 70° C. incubator for about 40 min. Then the slides were soaked in xylene for 15 min, and then soaked in anhydrous ethanol, 95% ethanol and 75% ethanol for 5 min each for gradient hydration.

2) Removing Endogenous Peroxidase

The slides were soked in 3% hydrogen peroxide for about 15 min to remove endogenous catalase in the tissue, and then washed with PBS buffer for three times, 5 min each time.

3) Antigen Retrieval

The antigen retrieval working solution (pH 6.0) was added in burning water. The slides were put into the retrieval solution, heated for about 10 min under the highest pressure, then the lid was opened to let the slides cool to room temperature naturally.

4) Blocking and Antibody Incubation

When cooled to room temperature, the slides were washed with PBS buffer for three times, 5 min each time, then 10% goat serum/PBS blocking solution was added dropwise on the specimens, and the slides were allowed to stand in a wet box at room temperature to block for 1 h. After that, the target protein antibody CAN001 (1:200-800) was added dropwise on the specimens, each slide was added dropwise with about 50 μL, and then the slides were placed in a wet box at 4° C. overnight and then washed with PBS buffer for three times, 5 min each time. 50 μL (1:200) of goat anti-mouse secondary antibody were added dropwise, and the slides were placed in a wet box and allowed to stand at room temperature for 1 h, and washed with PBS buffer for three times, 5 min each time.

5) DAB Color Development 1 to 2 drops of DAB chromogenic solution were added dropwise on each tissue slide, and a staining degree was observed under a microscope at the same time. When the staining degree was moderate, PBS buffer was added to stop the reaction, then the nucleus was counterstained with hematoxylin for 30 s, and then the reaction was stopped with PBS buffer.

6) Slide Mounting

A slide mounting medium was added dropwise next to the tissue, and then the tissue was covered with a square coverslip. In order to avoid bubbles, one side should be leveled first, then the other side. Finally, the coverslip was gently pressed several times, and the slide was mounted and air-dried for 24 h.

Figure 4:
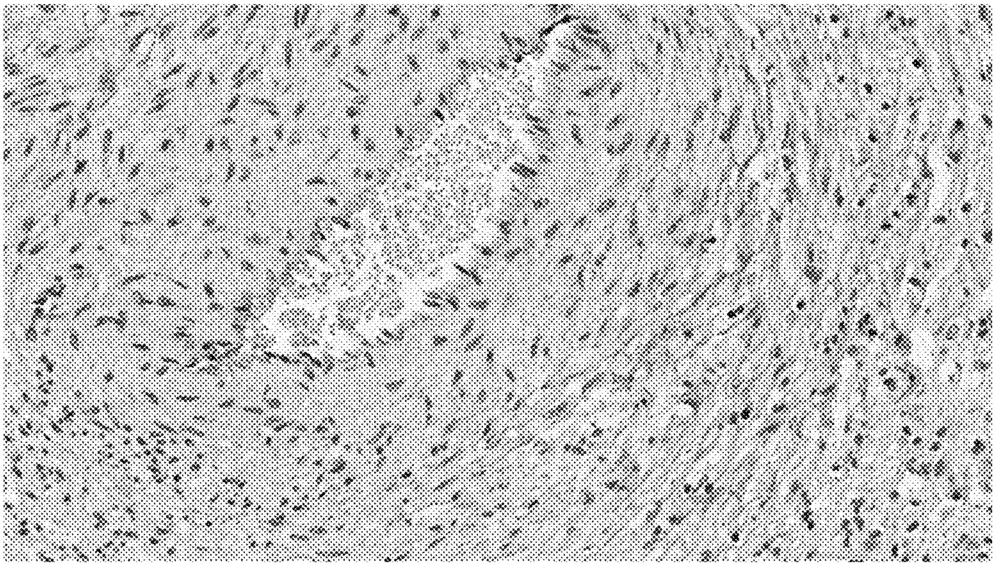
FIG. 4 shows IHC staining of human placenta with CAN001.

IHC staining of human placenta with CAN001 antibody is shown in FIG. 4.

Figure 5:
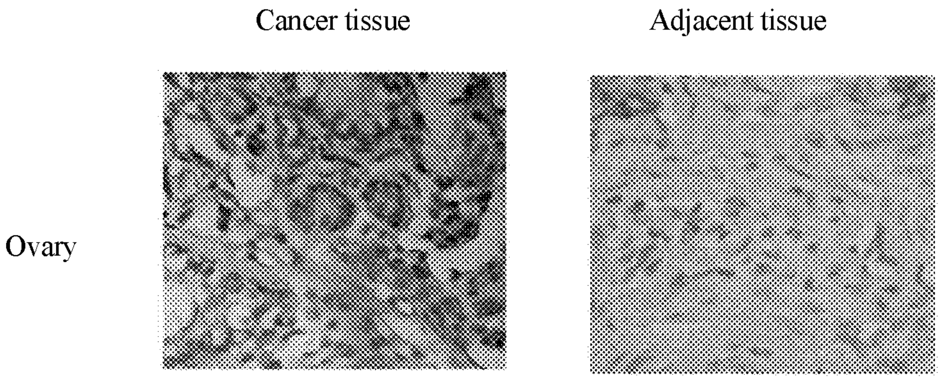
FIG. 5 shows IHC staining of ovarian cancer tissue and adjacent tissue with CAN001.

IHC staining of ovarian cancer tissue and adjacent tissue with CAN001 antibody is shown in FIG. 5.

Example 6: Preparation of CAN001 Antibody-Drug Conjugate

Antibody CAN001 (1,039.2 μL, 7.66 mg/mL) was diluted with PBS buffer (660.0 μL, pH=7) to obtain 1,699.2 μL of CAN001 antibody solution with a concentration of 4.68 mg/mL. TCEP (tris(2-carboxyethyl)phosphine) in PBS buffer (14.7 μL, 2.5 mM, pH=7) was added in the obtained CAN001 antibody solution, and the resulting solution was swirled gently and incubated at 37° C. for 2 h. Linker payload MC-MIVIAF (Maleimidocaproyl monomethylauristatin F) (136.5 μL, 3.5 mM in DMSO) was added, and the solution was swirled gently and kept at 25° C. for 1 h to obtain a crude sample. The crude sample was purified by illustra NAP-10 column (GE Healthcare) and filtered through 0.25 μm microfilter to afford the final antibody-drug conjugate CAN001-MC-MMAF, 3.1 mL, 2.56 mg/mL, DAR (drug-antibody ratio)=5.95, UmAb % (percentage of unconjugated antibody)=1.3%, and Agg % (percentage of polymerized antibody)=1.6%.

Structural formula of CAN001-MC-MMAF is shown in Formula 1.

Figure 6:
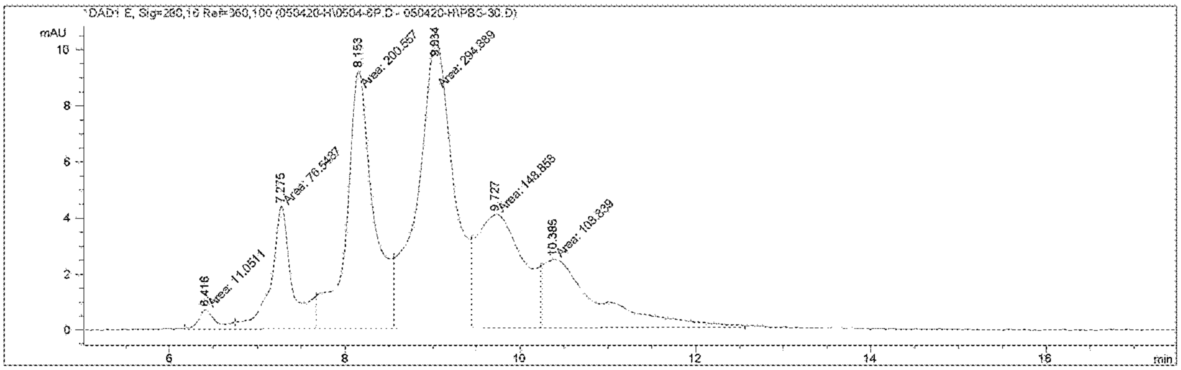
FIG. 6 shows hydrophobic interaction chromatography (HIC) of CAN001-MC-MMAF.

Hydrophobic interaction chromatography of CAN001-MC-MMAF is shown in FIG. 6.

Figure 7:
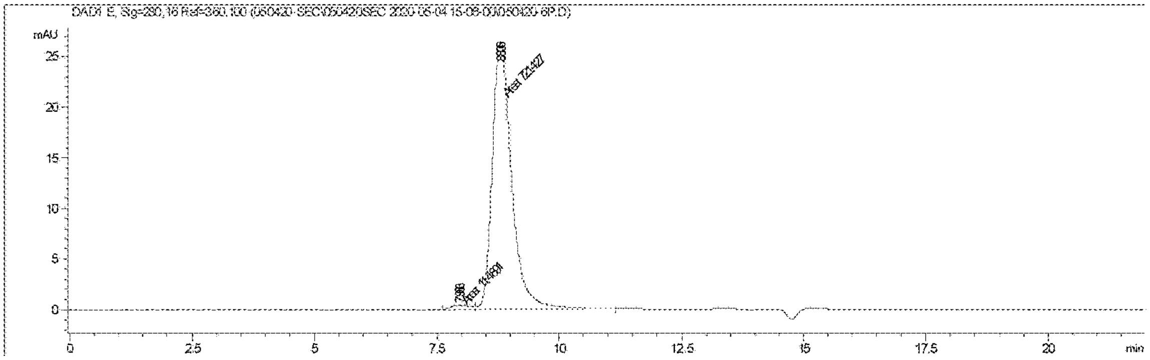
FIG. 7 shows size exclusion chromatography (SEC) of CAN001-MC-MMAF.

Size exclusion chromatography (SEC) of CAN001-MC-MMAF is shown in FIG. 7.

(Formula 1)

CAN001 antibody

Maleimidocaproyl (me)

Monomethylauristatin F (MMAF)

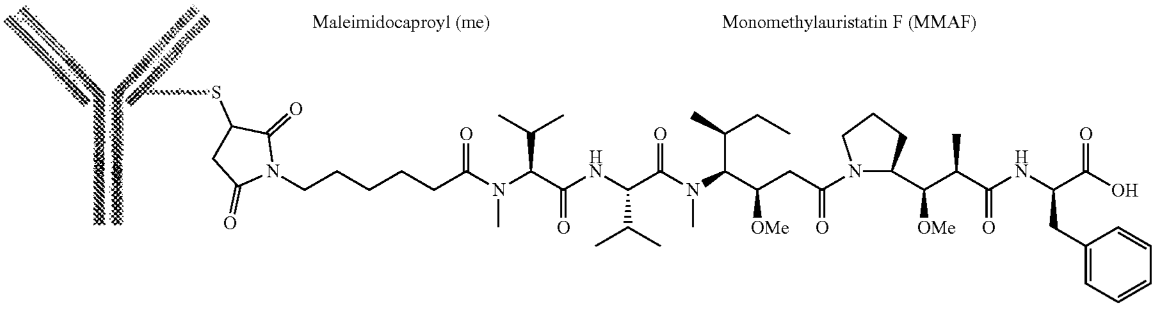

Example 7: Cell Killing Assay of CAN001 Antibody-Drug Conjugate

In this example, the anti-cancer effect of CAN001 antibody-drug conjugate was tested with CellTiter-Glo cell viability assay in a 96-well plate.

Human ovarian cancer cell lines: OVCAR-3, A2780, and 3A0, all from ATCC.

Cells were seeded in a 96-well cell culture plate with 1,000 cells per well, and the total amount of the culture medium per well was controlled to 200 μL. After the cells adhered to the wall, the cells were treated with corresponding drugs, and the drugs were withdrawn at different time points (0, 24 h, 48 h, 72 h and 96 h), and MTS detection solution (10 μL MTS reagent+190 μL complete medium) (MTS cell proliferation kit (colorimetry) from AmyJet Scientific) was added. Then, the 96-well cell culture plate was incubated in a $CO_2$ cell incubator for about 2 h away from light. Then, the cell culture plate was taken out and was measured at a wavelength of 492 nm to determine the absorbances of different groups of cells.

% inhibition and IC50 of each compound were calculated with XLFit curve fitting software. The results are shown in Table 1.

TABLE 1

| | IC50 (μM) | | |
|---|---|---|---|
| Cell line | CAN001 | MMAF | CAN001-MC-MMAF |
| OVCAR-3 | >1 | 0.205 | 0.107 |
| A2780 | | 0.223 | 0.062 |
| 3AO | | 0.301 | 0.107 |

Table 1 shows that the CAN001 antibody-drug conjugate CAN001-MC-MMAF had significantly higher killing effect on ovarian cancer cells than that of MMAF.

The invention claimed is:

1. An antibody or an antigen-binding fragment thereof that specifically binds to a human follicle-stimulating hormone receptor (FSHR), wherein the antibody or the antigen-binding fragment thereof comprises:

a light chain variable region comprising a complementarity-determining region (CDR) 1 having the amino acid sequence of SEQ ID NO: 6, a CDR2 having the amino acid sequence of SEQ ID NO: 7, and a CDR3 having the amino acid sequence of SEQ ID NO: 8, and a heavy chain variable region comprising a CDR1 having the amino acid sequence of SEQ ID NO: 10, a CDR2 having the amino acid sequence of SEQ ID NO: 11, and a CDR3 having the amino acid sequence of SEQ ID NO: 12.

2. The antibody or the antigen-binding fragment thereof according to claim 1, wherein the antibody or the antigen-binding fragment thereof comprises a light chain variable region and a heavy chain variable region; and wherein the light chain variable region comprises the amino acid sequence shown in SEQ ID NO: 5, or an amino acid sequence with at least 90% identity with the amino acid sequence shown in SEQ ID NO: 5, or an amino acid sequence with one or more conservative amino acid substitutions compared with the amino acid sequence shown in SEQ ID NO: 5; and/or the heavy chain variable region comprises the amino acid sequence shown in SEQ ID NO: 9, or an amino acid sequence with at least 90% identity with the amino acid sequence shown in SEQ ID NO: 9, or an amino acid sequence with one or more conservative amino acid substitutions compared with the amino acid sequence shown in SEQ ID NO: 9.

3. The antibody or the antigen-binding fragment thereof according to claim 1, wherein the antibody or the antigen-binding fragment thereof comprises a light chain and a heavy chain; and wherein the light chain comprises the amino acid sequence shown in SEQ ID NO: 3, or an amino acid sequence with at least 90% identity with the amino acid sequence shown in SEQ ID NO: 3, or an amino acid sequence with one or more conservative amino acid substitutions compared with the amino acid sequence shown in SEQ ID NO: 3; and/or the heavy chain comprises the amino acid sequence shown in SEQ ID NO: 4, or an amino acid sequence with at least 90% identity with the amino acid sequence shown in SEQ ID NO: 4, or an amino acid sequence with one or more conservative amino acid substitutions compared with the amino acid sequence shown in SEQ ID NO: 4.

4. A pharmaceutical composition comprising the antibody or the antigen-binding fragment thereof according to claim 1 and a pharmaceutically acceptable carrier.

5. An antibody-drug conjugate obtained by coupling the antibody or the antigen-binding fragment thereof according to claim 1 with a cytotoxic drug via a linker.

6. The antibody-drug conjugate according to claim 5, wherein the cytotoxic drug is a chemotherapeutic agent or a toxin; and/or the linker is maleimidocaproyl or an analogue thereof; and/or the antibody-drug conjugate has an average drug-antibody ratio (DAR) in a range of 1-10.

7. The antibody-drug conjugate according to claim 5, wherein the cytotoxic drug is a chemotherapeutic agent or an auristatin toxin; and/or the linker is maleimidocaproyl or an analogue thereof; and/or the antibody-drug conjugate has an average DAR in a range of 1-10.

8. A pharmaceutical composition comprising the antibody-drug conjugate according to claim 5 and a pharmaceutically acceptable carrier.

9. A method for inhibiting growth of a cancer cell that expresses FSHR, comprising contacting the cancer cell with the antibody-drug conjugate according to claim 5.

10. A method for treating a cancer that expresses FSHR in a patient, comprising administering a therapeutically effective amount of the antibody-drug conjugate according claim 5 to the patient.

11. The method according to claim 10, further comprising administering an additional therapeutic agent to the patient.

12. The method according to claim 11, wherein the additional therapeutic agent is a cytotoxic agent.

13. A nucleic acid molecule encoding the antibody or the antigen-binding fragment thereof according to claim 1.

14. The nucleic acid molecule according to claim 13, wherein the nucleic acid molecule comprises:

the nucleic acid fragment shown in positions 130-168 in SEQ ID NO: 1;

the nucleic acid fragment shown in positions 214-234 in SEQ ID NO: 1;

the nucleic acid fragment shown in positions 331-357 in SEQ ID NO: 1;

the nucleic acid fragment shown in positions 154-168 in SEQ ID NO: 2;

the nucleic acid fragment shown in positions 211-261 in SEQ ID NO: 2;

the nucleic acid fragment shown in positions 358-378 in SEQ ID NO: 2;

the nucleic acid fragment shown in positions 64-405 in SEQ ID NO: 1;

the nucleic acid fragment shown in positions 64-441 in SEQ ID NO: 2;

the nucleic acid fragment shown in SEQ ID NO: 1; or the nucleic acid fragment shown in SEQ ID NO: 2.

15. An expression cassette or a recombinant vector comprising the nucleic acid molecule according to claim 13.

16. A recombinant cell or a recombinant microorganism comprising the nucleic acid molecule according to claim 13.

17. A method for preparing the antibody or the antigen-binding fragment thereof according to claim 1, wherein the method comprises culturing a recombinant cell comprising a nucleic acid molecule encoding the antibody or the antigen-binding fragment thereof under a condition suitable for expression of the nucleic acid molecule.

* * * * *

SEQUENCE LISTING

<160> NUMBER OF SEQ ID NOS: 14

<210> SEQ ID NO 1
<211> LENGTH: 714
<212> TYPE: DNA
<213> ORGANISM: Artificial Sequence
<220> FEATURE:
<223> OTHER INFORMATION: Light chain DNA sequence

<400> SEQUENCE: 1
atggccctcc ctgtcaccgc cctgctgctt ccgctggctc ttctgctcca cgccgctcgg 60
ccccagatag tacttacgca atcacccgtc ataatgagcg catcccctgg tgaaaaggtt 120
actctgacat gctctgcgtc ttccagcgtg agtagttctt atctctattg gtatcagcaa 180
aaacccggat cttctagtaa attgtggata tattctacgt ctaatcttgc gtcaggagtg 240
cctgctcggt tttctgggtc cgggtccggg accagctata gtttgactat aagtagtatg 300
gaggcggagg acgcagctag ctacttttgc catcaatgga gctcctatcc tcctaccttt 360
gggggcggaa ccaaattgga aatcaaaaga gccgacgcgg cacccactgt atctatcttc 420
ccaccctcat cagaacagct cacttcaggc ggcgccagtg tggtgtgttt cctcaacaac 480
ttctatccta aagacataaa tgtaaaatgg aaaatagacg gtagcgagcg gcaaaacggg 540
gtgctgaact catggacgga ccaagattcc aaggattcta cctattcaat gagttctaca 600
ttgacactta cgaaagacga atacgagcgc cacaattcct atacgtgcga agcaacgcac 660
aaaacctcca cttccccgat tgtgaagtcc ttcaatagga atgaatgttg ataa 714

<210> SEQ ID NO 2
<211> LENGTH: 1404
<212> TYPE: DNA
<213> ORGANISM: Artificial Sequence
<220> FEATURE:
<223> OTHER INFORMATION: Heavy chain DNA sequence

<400> SEQUENCE: 2
atggagtttg ggctcagttg ggtctttctc gtggcactgt ttcgcggggt acagtgcgct 60
agccaagtac aactgcaaca accaggcgcg gagctcgtta aaccgggggc gagcgtcaac 120
cttagctgca aagcctccgg ttataccttt acaagttact ggatgcactg ggtgaagcag 180
cgaccagggc aaggacgcga atggatcggg gaaataaatc caaggaacgg cagaacgaat 240
tacaacgaga agttcaaatc caaggcgacg ttgacggtgg acaaatcctc ttcaactgct 300
tatatgcagc tcagttctct gacaagcgag gatagtgccg tgtactgttg cgccaggttg 360
tctgtggggt tcgcctactg gggcagggc acgctcgtta cagtctctgc ggccaagacg 420
actgcgcctt cagtatatcc actggctccg gtgtgcggag atacgacagg tagttctgta 480
actttgggat gcctcgttaa gggttatttc ccggagccgg tcaccttgac gtggaactcc 540
ggatcactct cctcaggggt acatacattt ccagcggttt tgcagagcga cctctacaca 600
ctcagtagca gtgtaaccgt tacctcatcc acatggccta gccagagtat cacgtgcaat 660
gttgcacacc cggcaagttc taccaaggtg gacaaaaaac tcgagcctag aggaccgacg 720
ataaagccct gtccgccttg caaatgtccg gcacctaacg ctgctggtgg cccctctgtt 780
tttatatttc cgccaaaaat taaggacgtc ctcatgatca gtctgagccc tatagtcacg 840
tgtgtggtgg tagatgtctc tgaagacgat cccgacgtac agatttcatg gttcgtgaac 900
aatgtggagg ttcacacagc ccaaacacag acacaccgcg aagattacaa tagtacactg 960
cgggtagtct ctgccctccc aatacaacac caggactgga tgagcgggaa agagttcaag 1020
tgcaaagtca ataacaaaga cctgggagcg ccgatagaaa gaactataag taaaccaaag 1080
gggagcgtaa gagcgcccca agtgtatgtc ctccctcctc ccgaagagga aatgaccaag 1140
aaacaagtta ctctcacatg catggtaacc gatttcatgc ctgaagacat atacgtagag 1200
tggaccaaca acgggaagac agaattgaac tacaagaata cagagcccgt tctcgattct 1260
gatggctcct actttatgta tagcaaactc cgggtggaaa aaaagaattg ggtcgaaaga 1320
aacagttatt catgttctgt tgttcacgag ggtttgcata accatcatac gacgaaatct 1380
ttttccagaa ccccaggaaa atga 1404

<210> SEQ ID NO 3
<211> LENGTH: 236
<212> TYPE: PRT
<213> ORGANISM: Artificial Sequence
<220> FEATURE:
<223> OTHER INFORMATION: Light chain amino acid sequence

<400> SEQUENCE: 3

Met Ala Leu Pro Val Thr Ala Leu Leu Leu Pro Leu Ala Leu Leu Leu
1 5 10 15

His Ala Ala Arg Pro Gln Ile Val Leu Thr Gln Ser Pro Val Ile Met
20 25 30

Ser Ala Ser Pro Gly Glu Lys Val Thr Leu Thr Cys Ser Ala Ser Ser
35 40 45

Ser Val Ser Ser Ser Tyr Leu Tyr Trp Tyr Gln Gln Lys Pro Gly Ser
50 55 60

Ser Ser Lys Leu Trp Ile Tyr Ser Thr Ser Asn Leu Ala Ser Gly Val
65 70 75 80

Pro Ala Arg Phe Ser Gly Ser Gly Ser Gly Thr Ser Tyr Ser Leu Thr
85 90 95

Ile Ser Ser Met Glu Ala Glu Asp Ala Ala Ser Tyr Phe Cys His Gln
100 105 110

Trp Ser Ser Tyr Pro Pro Thr Phe Gly Gly Gly Thr Lys Leu Glu Ile
115 120 125

Lys Arg Ala Asp Ala Ala Pro Thr Val Ser Ile Phe Pro Pro Ser Ser
130 135 140

Glu Gln Leu Thr Ser Gly Gly Ala Ser Val Val Cys Phe Leu Asn Asn
145 150 155 160

Phe Tyr Pro Lys Asp Ile Asn Val Lys Trp Lys Ile Asp Gly Ser Glu
165 170 175

Arg Gln Asn Gly Val Leu Asn Ser Trp Thr Asp Gln Asp Ser Lys Asp

-continued

```
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Cys
225                 230                 235


<210> SEQ ID NO 4
<211> LENGTH: 467
<212> TYPE: PRT
<213> ORGANISM: Artificial Sequence
<220> FEATURE:
<223> OTHER INFORMATION: Heavy chain amino acid sequence

<400> SEQUENCE: 4

Met Glu Phe Gly Leu Ser Trp Val Phe Leu Val Ala Leu Phe Arg Gly
1               5                   10                  15

Val Gln Cys Ala Ser Gln Val Gln Leu Gln Gln Pro Gly Ala Glu Leu
            20                  25                  30

Val Lys Pro Gly Ala Ser Val Asn Leu Ser Cys Lys Ala Ser Gly Tyr
        35                  40                  45

Thr Phe Thr Ser Tyr Trp Met His Trp Val Lys Gln Arg Pro Gly Gln
    50                  55                  60

Gly Arg Glu Trp Ile Gly Glu Ile Asn Pro Arg Asn Gly Arg Thr Asn
65                  70                  75                  80

Tyr Asn Glu Lys Phe Lys Ser Lys Ala Thr Leu Thr Val Asp Lys Ser
                85                  90                  95

Ser Ser Thr Ala Tyr Met Gln Leu Ser Ser Leu Thr Ser Glu Asp Ser
            100                 105                 110

Ala Val Tyr Cys Cys Ala Arg Leu Ser Val Gly Phe Ala Tyr Trp Gly
        115                 120                 125

Gln Gly Thr Leu Val Thr Val Ser Ala Ala Lys Thr Thr Ala Pro Ser
    130                 135                 140

Val Tyr Pro Leu Ala Pro Val Cys Gly Asp Thr Thr Gly Ser Ser Val
145                 150                 155                 160

Thr Leu Gly Cys Leu Val Lys Gly Tyr Phe Pro Glu Pro Val Thr Leu
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Thr
        195                 200                 205

Ser Ser Thr Trp Pro Ser Gln Ser Ile Thr Cys Asn Val Ala His Pro
    210                 215                 220

Ala Ser Ser Thr Lys Val Asp Lys Lys Leu Glu Pro Arg Gly Pro Thr
225                 230                 235                 240

Ile Lys Pro Cys Pro Pro Cys Lys Cys Pro Ala Pro Asn Ala Ala Gly
                245                 250                 255

Gly Pro Ser Val Phe Ile Phe Pro Pro Lys Ile Lys Asp Val Leu Met
            260                 265                 270

Ile Ser Leu Ser Pro Ile Val Thr Cys Val Val Val Asp Val Ser Glu
        275                 280                 285

Asp Asp Pro Asp Val Gln Ile Ser Trp Phe Val Asn Asn Val Glu Val
    290                 295                 300

His Thr Ala Gln Thr Gln Thr His Arg Glu Asp Tyr Asn Ser Thr Leu
```

-continued

```
305                 310                 315                 320

Arg Val Val Ser Ala Leu Pro Ile Gln His Gln Asp Trp Met Ser Gly
                325                 330                 335

Lys Glu Phe Lys Cys Lys Val Asn Asn Lys Asp Leu Gly Ala Pro Ile
            340                 345                 350

Glu Arg Thr Ile Ser Lys Pro Lys Gly Ser Val Arg Ala Pro Gln Val
        355                 360                 365

Tyr Val Leu Pro Pro Pro Glu Glu Glu Met Thr Lys Lys Gln Val Thr
    370                 375                 380

Leu Thr Cys Met Val Thr Asp Phe Met Pro Glu Asp Ile Tyr Val Glu
385                 390                 395                 400

Trp Thr Asn Asn Gly Lys Thr Glu Leu Asn Tyr Lys Asn Thr Glu Pro
                405                 410                 415

Val Leu Asp Ser Asp Gly Ser Tyr Phe Met Tyr Ser Lys Leu Arg Val
            420                 425                 430

Glu Lys Lys Asn Trp Val Glu Arg Asn Ser Tyr Ser Cys Ser Val Val
        435                 440                 445

His Glu Gly Leu His Asn His His Thr Thr Lys Ser Phe Ser Arg Thr
    450                 455                 460

Pro Gly Lys
465


<210> SEQ ID NO 5
<211> LENGTH: 114
<212> TYPE: PRT
<213> ORGANISM: Artificial Sequence
<220> FEATURE:
<223> OTHER INFORMATION: Amino acid sequence of light chain variable
      region

<400> SEQUENCE: 5

Gln Ile Val Leu Thr Gln Ser Pro Val Ile Met Ser Ala Ser Pro Gly
1               5                   10                  15

Glu Lys Val Thr Leu Thr Cys Ser Ala Ser Ser Ser Val Ser Ser Ser
            20                  25                  30

Tyr Leu Tyr Trp Tyr Gln Gln Lys Pro Gly Ser Ser Ser Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Pro Thr Phe Gly Gly Gly Thr Lys Leu Glu Ile Lys Arg Ala Asp Ala
            100                 105                 110

Ala Pro


<210> SEQ ID NO 6
<211> LENGTH: 13
<212> TYPE: PRT
<213> ORGANISM: Artificial Sequence
<220> FEATURE:
<223> OTHER INFORMATION: Amino acid sequence of light chain CDR1

<400> SEQUENCE: 6

Cys Ser Ala Ser Ser Ser Val Ser Ser Ser Tyr Leu Tyr
1               5                   10
```

-continued

<210> SEQ ID NO 7
<211> LENGTH: 7
<212> TYPE: PRT
<213> ORGANISM: Artificial Sequence
<220> FEATURE:
<223> OTHER INFORMATION: Amino acid sequence of light chain CDR2

<400> SEQUENCE: 7

Ser Thr Ser Asn Leu Ala Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Amino acid sequence of light chain CDR3

<400> SEQUENCE: 8

His Gln Trp Ser Ser Tyr Pro Pro Thr
1               5

<210> SEQ ID NO 9
<211> LENGTH: 126
<212> TYPE: PRT
<213> ORGANISM: Artificial Sequence
<220> FEATURE:
<223> OTHER INFORMATION: Amino acid sequence of heavy chain variable region

<400> SEQUENCE: 9

Gln Val Gln Leu Gln Gln Pro Gly Ala Glu Leu Val Lys Pro Gly Ala
1               5                   10                  15

Ser Val Asn Leu Ser Cys Lys Ala Ser Gly Tyr Thr Phe Thr Ser Tyr
            20                  25                  30

Trp Met His Trp Val Lys Gln Arg Pro Gly Gln Gly Arg Glu Trp Ile
        35                  40                  45

Gly Glu Ile Asn Pro Arg Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Cys Cys
                85                  90                  95

Ala Arg Leu Ser Val Gly Phe Ala Tyr Trp Gly Gln Gly Thr Leu Val
            100                 105                 110

Thr Val Ser Ala Ala Lys Thr Thr Ala Pro Ser Val Tyr Pro
        115                 120                 125

<210> SEQ ID NO 10
<211> LENGTH: 5
<212> TYPE: PRT
<213> ORGANISM: Artificial Sequence
<220> FEATURE:
<223> OTHER INFORMATION: Amino acid sequence of heavy chain CDR1

<400> SEQUENCE: 10

Ser Tyr Trp Met His
1               5

<210> SEQ ID NO 11
<211> LENGTH: 17
<212> TYPE: PRT
<213> ORGANISM: Artificial Sequence -continued
<220> FEATURE:
<223> OTHER INFORMATION: Amino acid sequence of heavy chain CDR2

<400> SEQUENCE: 11

Glu Ile Asn Pro Arg Asn Gly Arg Thr Asn Tyr Asn Glu Lys Phe Lys
1 5 10 15

Ser

<210> SEQ ID NO 12
<211> LENGTH: 7
<212> TYPE: PRT
<213> ORGANISM: Artificial Sequence
<220> FEATURE:
<223> OTHER INFORMATION: Amino acid sequence of heavy chain CDR3

<400> SEQUENCE: 12

Leu Ser Val Gly Phe Ala Tyr
1 5

<210> SEQ ID NO 13
<211> LENGTH: 28
<212> TYPE: DNA
<213> ORGANISM: Artificial Sequence
<220> FEATURE:
<223> OTHER INFORMATION: Primer FSHR-F

<400> SEQUENCE: 13
gtttccacaa ccatggccct gctcctgg 28

<210> SEQ ID NO 14
<211> LENGTH: 49
<212> TYPE: DNA
<213> ORGANISM: Artificial Sequence
<220> FEATURE:
<223> OTHER INFORMATION: Primer FSHR-R

<400> SEQUENCE: 14
ggttgattaa ctcgagttag ttttgggcta aatgacttag agggacaag 49